(12) United States Patent
Bouzid et al.

(10) Patent No.: US 8,410,454 B2
(45) Date of Patent: Apr. 2, 2013

(54) HIGH DYNAMIC RANGE SCANNING WITH REDUCED CHANNEL CROSS-TALK

(75) Inventors: Ahmed Bouzid, Lincoln, NE (US); Christopher J. Lesiak, Lincoln, NE (US)

(73) Assignee: LI-COR, Inc., Lincoln, NE (US)

( * ) Notice: Subject to any disclaimer, the term of this patent is extended or adjusted under 35 U.S.C. 154(b) by 0 days.

(21) Appl. No.: 13/106,776

(22) Filed: May 12, 2011

(65) Prior Publication Data

US 2011/0278470 A1  Nov. 17, 2011

Related U.S. Application Data

(60) Provisional application No. 61/334,100, filed on May 12, 2010.

(51) Int. Cl.
  *G01N 21/64* (2006.01)
(52) U.S. Cl. .................................................. 250/458.1
(58) Field of Classification Search ............. 250/458.1
  See application file for complete search history.

(56) References Cited

U.S. PATENT DOCUMENTS

| | | | |
|---|---|---|---|
| 5,491,343 A * | 2/1996 | Brooker | 250/458.1 |
| 6,320,196 B1 * | 11/2001 | Dorsel et al. | 250/458.1 |
| 6,495,812 B1 | 12/2002 | Wurm et al. | |
| 6,806,460 B2 | 10/2004 | Corson | |
| 6,870,166 B2 | 3/2005 | Curry et al. | |
| 6,952,008 B2 | 10/2005 | Corson | |
| 7,054,003 B2 | 5/2006 | Dorsel | |
| 7,361,472 B2 | 4/2008 | Yguerabide et al. | |
| 7,362,432 B2 | 4/2008 | Roth | |
| 7,463,357 B2 | 12/2008 | Kralik et al. | |
| 2004/0121483 A1 | 6/2004 | Corson et al. | |
| 2007/0178480 A1 | 8/2007 | Corson et al. | |
| 2008/0030628 A1 * | 2/2008 | Lundquist et al. | 348/751 |

FOREIGN PATENT DOCUMENTS

JP   2003-185927 A   7/2003

OTHER PUBLICATIONS

Berndt, K., Phase and Modulation degree fluorometer for rapid spectroscopy contains avalanche diode detector modulated at low frequency synchronously w.r.t. stimulation modulation, Oct. 21, 1985, DERWENT Publication of East German Abstract.*

* cited by examiner

*Primary Examiner* — David Porta
*Assistant Examiner* — Hugh H Maupin
(74) *Attorney, Agent, or Firm* — Leydig, Voit & Mayer, LLP; Gerald T. Gray

(57) ABSTRACT

A multi-channel scanning system adapted to implement a low channel cross-talk, extra-wide dynamic range scanning method by scanning the same location more than once, wherein at least one time, the power of the excitation light and detector gain are set to High for at least one of the channels and Low for at least one of the other channels and different settings are used in subsequent scans. The scans of the same channel taken with different High and Low settings are merged together to produce one wider dynamic range image.

32 Claims, 5 Drawing Sheets

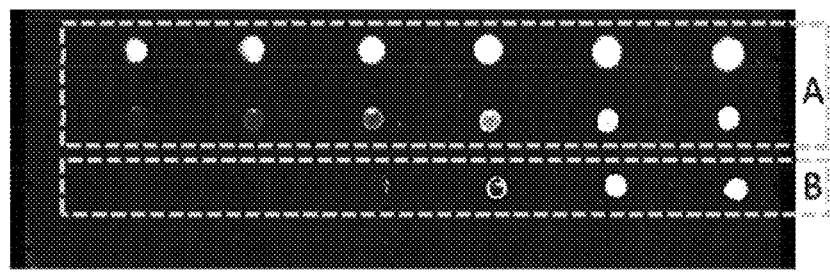
Figure 1a: 2X IRDye® 800CW dilutions spotted on a nitrocellulose membrane and scanned on an Odyssey®.
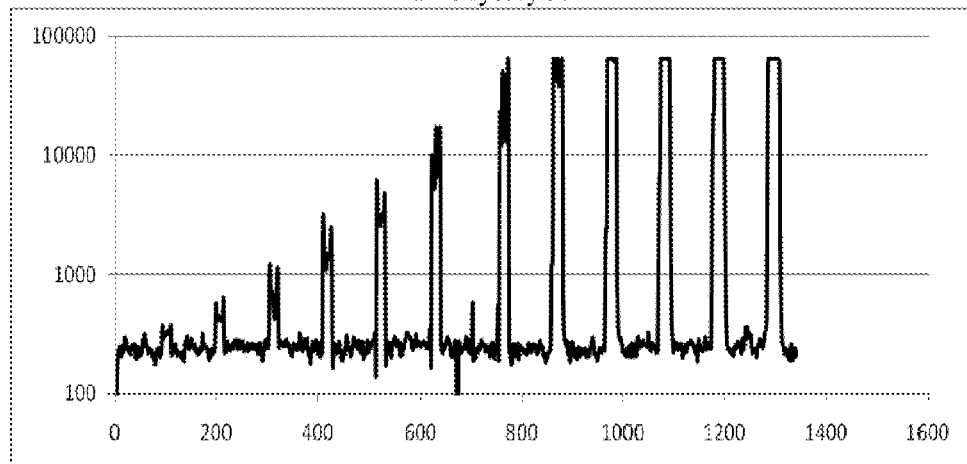
Figure 1b: A line-profile across the rows of region "A" of Figure 1a.

|  | Channel 1 | | Channel 2 | |
| --- | --- | --- | --- | --- |
|  | Laser 1 | Detector 1 | Laser 2 | Detector 2 |
| Scan 1 | High | High | Low | Low |
| Scan 2 | Low | Low | High | High |
|  |  | ↓ |  | ↓ |
|  |  | Ch1_merged |  | Ch2_merged |

|  | Channel 1 | | Channel 2 | |
| --- | --- | --- | --- | --- |
|  | Laser 1 | Detector 1 | Laser 2 | Detector 2 |
| Scan 1 | High | High | Low | Low |
| Scan 2 | Mid | Mid | Mid | Mid |
| Scan 3 | Low | Low | High | High |
|  |  | ↓ |  | ↓ |
|  |  | Ch1_merged |  | Ch2_merged |

|        | Channel 1 | | Channel 2 | | Channel 3 | |
|--------|-----------|----------|-----------|----------|-----------|----------|
|        | Laser 1   | Detector 1 | Laser 2 | Detector 2 | Laser 3 | Detector 3 |
| Scan 1 | High | High | Low  | Low  | Low  | Low  |
| Scan 2 | Low  | Low  | High | High | Low  | Low  |
| Scan 3 | Low  | Low  | Low  | Low  | High | High |
|        |      | ↓ Ch1_merged |      | ↓ Ch2_merged |      | ↓ Ch3_merged |

Figure 5a

|        | Channel 1 | | Channel 2 | | Channel 3 | |
|--------|-----------|----------|-----------|----------|-----------|----------|
|        | Laser 1   | Detector 1 | Laser 2 | Detector 2 | Laser 3 | Detector 3 |
| Scan 1 | High | High | Low  | Low  | Mid  | Mid  |
| Scan 2 | Mid  | Mid  | High | High | Low  | Low  |
| Scan 3 | Low  | Low  | Mid  | Mid  | High | High |
|        |      | ↓ Ch1_merged |      | ↓ Ch2_merged |      | ↓ Ch3_merged |

Figure 5b

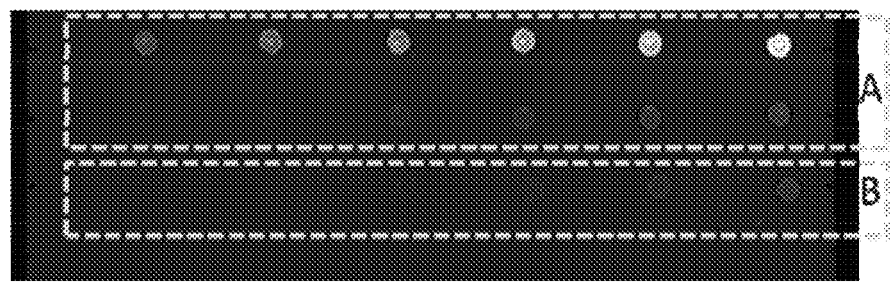
Figure 6a: Same dilution of Figure 1a imaged by an embodiment.
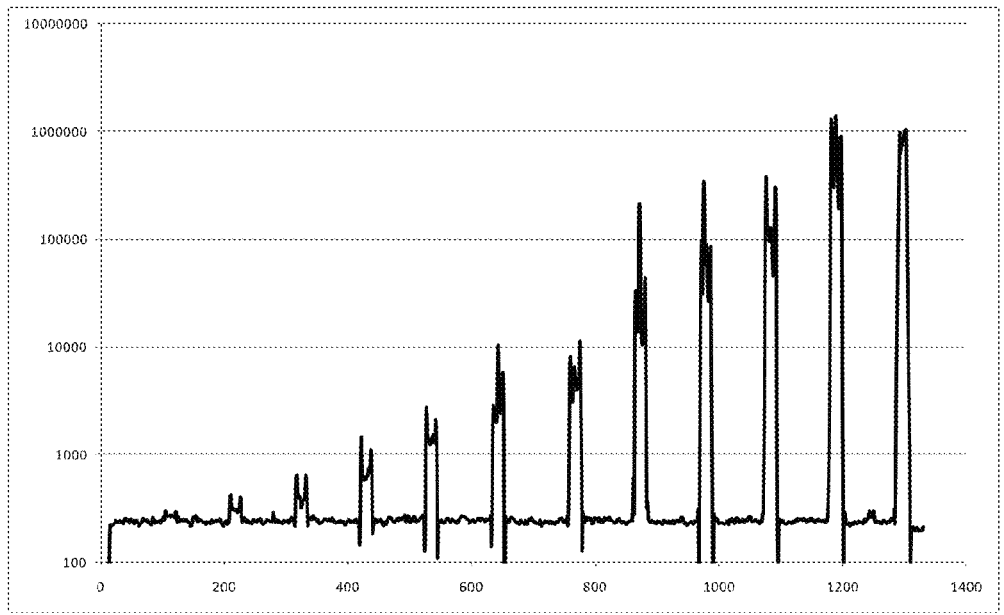
Figure 6b: A line-profile across the rows of region "A" of Figure 6a

HIGH DYNAMIC RANGE SCANNING WITH REDUCED CHANNEL CROSS-TALK

CROSS-REFERENCES TO RELATED APPLICATIONS

This application claims the benefit of U.S. Provisional Application Ser. No. 61/334,100, filed May 12, 2010, the disclosure of which is incorporated herein by reference in its entirety.

BACKGROUND

The present invention relates generally to fluorescence detection systems, and more particularly to reducing or eliminating cross-talk and extending the dynamic range of such systems.

Optical fluorescence detection technologies are becoming more and more key tools for advancing bioscience discoveries. And, as the pace of scientific research increases, the demand for sensitivity, quantification, speed, and automation of such tools increases. One detection system, the LI-COR Odyssey® scanner (see, e.g., U.S. Pat. No. 6,495,812), uses a sensitive optical detection system, optimized for the Near Infra-Red spectral region, where it is well known that most biological samples and most materials have low auto-fluorescence, and delivers the sensitivity needed for high demanding applications. The system has nearly 15-bit (>4 orders of magnitude) of dynamic range within the same scan. This is more than sufficient for most applications. However, the levels of fluorescence signals can vary significantly from application to application and therefore there is currently a need to select a gain setting that allows for capturing most of the dynamic range without much saturation. FIG. 1a shows an image of a 2× dilution with saturated spots. The rows of region "A" are of the same 800-channel dilution. FIG. 1b shows a profile that runs across the dilution (i.e. both rows) and indicates that 4 spots are totally saturated and one spot partially saturated.

The region labeled "B" shows some channel cross-talk from the 700-channel that results in saturating the 800-detector. At the shown saturated spot in region "B", there exists another dilution, but with a 700-dye label (IRDye® 700DX, which is excitable only very minimally by the 780 nm laser). But, the saturation of the 800 detector at those locations is an indication of a relatively strong fluorescence signal resulting from the 700 excitation (i.e. 680 nm laser). A similar channel cross-talk occurs from the 800 excitation into the 700-channel detection. Reducing such a cross-talk enhances the sensitivity of both channels across the whole field.

Odyssey® uses pre-set excitation laser power and Avalanche Photo-Diodes (APDs) as detectors for detecting emitted fluorescence. The signal level provided by the system depends on the laser power, the fluorescence concentration, detection collection efficiency, and detector gain settings. The former three are set by design and the gain setting is adjustable. This system-level gain includes an amplification gain of the APD itself followed by an electronic amplification stage. Currently, the range of gain settings available takes advantage of both components, and allows for more than 1000× system-level gain change. It is desirable, however, to maintain the APD gain level at a single setting so that its sensitivity performance is maintained over the wider dynamic range. Fixing the APD gain leaves only the electronic amplification to adjust, which results in a limited extension of the dynamic range. Furthermore, relatively strong fluorescence signals can saturate the APD and in that case, the electronic gain can not result in any useful extension of the dynamic range. There is therefore a need to extend the dynamic range capability of a scanner, such as Odyssey®, without changing the sensitivity of the detector.

The Odyssey® scanning design benefits in a number of ways from exciting the same location of a sample with two laser colors. The optical filtering and the modulation-demodulation technique allows for efficient separation of emitted fluorescence stimulated by both lasers giving two images simultaneously: 700 and 800 channels. However, when the amount of emitted fluorescence is high, residual fluorescence leakage from one channel into another can result in limiting the dynamic range of the APD. For example, the 800-channel APD can receive leakage from 700-channel fluorescence than can saturate it even if there is no 800-channel fluorescence, and demodulating with the 800 laser modulation frequency does not help. This case is clearly shown in the spots in area "B" in FIG. 1a. The image is an 800-channel image and the shown spots contain 700-dye only, but with relatively high concentrations. It clearly shows the 800-channel detector is saturated even though there is no 800 fluorescence. This cross-channel effect can be reduced by changing the APD gain described above, but this affects its sensitivity to 800-fluorescence, the desired fluorescence in that channel. It is, therefore, desirable to minimize or eliminate this cross-channel effect while maintaining the APD gain setting at its, high, sensitive setting. It is further desirable to accomplish this together with extending the dynamic range of the system.

U.S. Pat. No. 7,463,357 extends the dynamic range of a chemical array reader by splitting the detection light into two light beams and detecting them with different types of detectors having overlapping dynamic ranges. This does not reduce the channel cross-talk described above and requires both detectors to have similar optimum operating gain settings. Furthermore, splitting the light into two beams effectively results in a reduction of the otherwise obtainable sensitivity. It is desirable to maintain or enhance the sensitivity, not reduce it. Corson (U.S. Pat. Nos. 6,952,008 and 6,806,460) also teaches a fluorescence detection technique based on the same idea of splitting the collected fluorescence light within a spectral range (color) into two portions and detecting them with detectors of different dynamic ranges and combing both measurements to produce an image with higher dynamic range.

U.S. Pat. No. 7,054,003 teaches how to read different regions of a chemical array with light of different intensities and simultaneously detecting light emitted from the different regions, as a way to image an array with a wide dynamic range. This does not solve the limitation described above, which desires to maintain the illumination of and detection from the same location. Applying the different intensity idea at the same location and detecting them both at the same time does not work with the same excitation and emission wavelength ranges and results in more of the channel cross-talk problem. Even if combined with other techniques, such as described by U.S. patent application Ser. No. 11/036,571, to split the beam into portions and detect them separately, requires adding other detectors and associated optics for each color, a costly endeavor.

U.S. Pat. No. 7,361,472 provides a method for extending the dynamic range of scattered light measurement based on measuring the same light multiple times using different filters to reduce signal levels and then combines the measurements using pre-determined filter optical density ratios. In addition to the fact that imaging in fluorescence presents different challenges that the invention does not address, the idea of re-measuring the same light by using filters to block part of the light being detected does not solve the channel cross-talk problem.

U.S. Pat. No. 6,870,166 and application Ser. No. 11/344,773 describe methods of extending the dynamic range of reading chemical array by scanning the array twice at different gain settings. Although, this avoids having to split the collected light into portion(s), it still does not work if detectors, such as APDs, are to be operated at the same optimized gain setting, as described above. Furthermore, this method does not change any channel cross-talk caused by simultaneous multi-color detection, such as desired here.

U.S. Pat. No. 6,320,196 presents a solution to dye cross-talk that can work for channel cross-talk, but it is based on spatially separating different color optics, i.e. focusing lasers at separate spots and collecting emitted fluorescence by separate optics and detectors. This does not have the advantage of compact, cost-effective of single-spot scanning and techniques that work for separated optics do not work for combined optics.

Therefore it is desirable to provide systems and methods that overcome the above and other problems. In particular, it is desirable to provide a significant increase in overall dynamic range and reduction in channel cross-talk while maintaining sensitivity and compactness of single-spot scanning.

BRIEF SUMMARY

The present invention provides systems and methods for reducing cross-talk in fluorescence detection systems as well as extending the dynamic range of such detection systems.

A multi-channel scanning system implements a low channel cross-talk, extra-wide dynamic range scanning method by scanning the same location more than once, wherein at least one time, the power of the excitation light and detector gain are set to High for at least one of the channels and Low for at least one of the other channels and different settings are used in subsequent scans. The scans of the same channel taken with different High and Low settings are merged together to produce one wider dynamic range image.

According to one embodiment, a method is provided for reducing or eliminating cross talk in a fluorescence detection system having two sources that emit illumination at different wavelengths, two detectors that detect at different wavelengths, and a sample platform having at least two fluorescent species, wherein a first fluorescent species absorbs light from a first illumination source and emits at a first fluorescence wavelength, and wherein a second fluorescent species absorbs light from a second illumination source and emits at a second fluorescence wavelength. The method typically includes a) in a first illumination and detection setting mode, wherein the first illumination source is set to a high power setting and a first detector is set to a high gain setting, and the second illumination source is set to a low power setting and a second detector is set to a low gain setting: i) illuminating at least one of a plurality of pixel locations of the sample platform with illumination from the first and second illumination sources, and ii) detecting a first intensity value for each detector, the first detector detecting at the first fluorescence wavelength, and the second detector detecting at the second fluorescence wavelength. The method also typically includes b) in a second illumination and detection setting mode, wherein the first illumination source is set to a low power setting and the first detector is set to a low gain setting, and the second illumination source is set to a high power setting and the second detector is set to a high gain setting: i) illuminating the at least one pixel location with illumination from the first and second illumination sources, and ii) detecting a second intensity value for each detector. The method typically includes c) for each detector, processing the first and second intensity values to produce a merged image value for the at least one pixel location. In certain aspects, for each source a ratio of the high power setting to the low power setting is about 2 or greater, or even 10 or greater, and wherein for each detector a ratio of the high gain setting to the low gain setting is about 2 or greater, or even 10 or greater. In certain aspects, processing includes performing a linear regression fit between the first and second intensity values to determine the merged image value for the pixel. For example, the slope of the resulting regression fit represents the merged image value for the pixel in certain aspects.

According to another embodiment, a fluorescence detection system is provided that typically includes a first illumination source that emits at a first illumination frequency, a second illumination source that emits at a second illumination frequency, a first detector element configured to detect radiation at a first fluorescence frequency, a second detector element configured to detect radiation at a second fluorescence frequency, and a target platform having a sample with two fluorescent species, wherein a first species absorbs illumination at the first illumination frequency and emits at the first fluorescence frequency, and wherein a second species absorbs illumination at the second illumination frequency and emits at the second fluorescence frequency. The system also typically includes optical elements configured to combine and focus illumination of the first and second sources onto the sample, and optical elements configured to direct and focus fluorescence light emitted by the sample onto the first and second detector elements. The system further typically includes an intelligence module, e.g., a processor, adapted to receive and process signals received from the first and second detectors. During typical operation, at least one pixel location on the sample platform is illuminated by the first and second sources in a first mode and in a second mode, and wherein fluorescence emitted by the first and second species is detected by the first and second detectors in the first mode and in the second mode. In the first mode the first illumination source is set to a high power setting and the first detector is set to a high gain setting, and the second illumination source is set to a low power setting and the second detector is set to a low gain setting, and in the second mode the first illumination source is set to a high power setting and the first detector is set to a high gain setting, and the second illumination source is set to a low power setting and the second detector is set to a low gain setting. Also, in the first mode, each detector outputs a first intensity value, and in the second mode, each detector outputs a second intensity value. The intelligence module, for each detector, processes the first and second intensity values to produce a merged image value for the at least one pixel location. In certain aspects, for each source a ratio of the high power setting to the low power setting is about 2 or greater, or even 10 or greater, and wherein for each detector a ratio of the high gain setting to the low gain setting is about 2 or greater, or even 10 or greater. In certain aspects, processing includes performing a linear regression fit between the first and second intensity values to determine the merged image value for the pixel. For example, the slope of the resulting regression fit represents the merged image value for the pixel in certain aspects.

In certain aspects the system further includes a display device for displaying a representation of the merged image value for the at least one pixel for each detector. In certain aspects, each of a plurality of pixel locations on the sample platform are illuminated by the first and second sources in the first mode and in the second mode, and fluorescence emitted by the first and second species is detected by the first and second detectors in the first mode and in the second mode, and the intelligence module, for each detector, processes the first and second intensity values to produce a merged image value for each of the plurality of pixel locations. In certain aspects, the system includes a display device for displaying a representation of the merged image values for some or all of the plurality of pixels for each detector.

According to yet another embodiment, a method is provided for reducing or eliminating cross talk in a fluorescence detection system having two sources that emit illumination at different wavelengths, a sample platform having at least two fluorescent species and two detection channels. The method typically includes a) setting the illumination power of a first source to a high power level and the illumination power of a second source to a low power level, b) setting the gain of a first detector to a high gain level and the gain of a second detector to a low gain level, c) illuminating at least one of a plurality of pixel locations of the sample platform with illumination from the first and second sources, wherein a first fluorescent species absorbs light from the first source and emits at a first fluorescence wavelength, and wherein a second fluorescent species absorbs light from the second source and emits at a second fluorescence wavelength, and d) detecting a first intensity value for each detection channel, wherein a first detector detects the first fluorescence wavelength and a second detector detects the second fluorescence wavelength. The method also typically includes, thereafter, e) setting the illumination power of the first source to a low power level and the illumination power of the second source to a high power level, f) setting the gain of the first detector to a low gain level and the gain of the second detector to a high gain level, g) illuminating the at least one pixel location with illumination from the first and second sources, and h) detecting a second intensity value for each channel. The method also typically includes, thereafter, i) for each channel, processing the first and second intensity values to produce a merged image value for the at least one pixel location. In certain aspects, for each source a ratio of the high power setting to the low power setting is about 2 or greater, or even 10 or greater, and wherein for each detector a ratio of the high gain level to the low gain level is about 2 or greater, or even 10 or greater. In certain aspects, processing includes performing a linear regression fit between the first and second intensity values to determine the merged image value for the pixel. For example, the slope of the resulting regression fit represents the merged image value for the pixel in certain aspects.

In certain aspects, the first and second sources are modulated at first and second modulation frequencies lower than the frequency of emitted illumination and the first and second detectors are de-modulated at the first and second modulation frequencies, respectively.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 1a shows an image of a 2× dilution with saturated spots; FIG. 1b shows a profile that runs across the dilution (i.e. both rows) and indicates that 4 spots are totally saturated and one spot partially saturated.

FIGS. 5a and 5b list example sets of settings for the scans and image groups to merge together for a 3-channel system scan according to one embodiment.

FIG. 6a shows a merged scan of the same dilutions of FIG. 1a obtained by one embodiment having a High/Low ratio of 135×; FIG. 6b shows a line profile across the dilution in region "A".

DETAILED DESCRIPTION

The present invention provides systems and methods for reducing cross-talk in fluorescence detection systems as well as extending the dynamic range of such detection systems.

Systems and methods are described below in reference to two-color scanning (e.g., 2 channels), such as implemented in Odyssey®, but it should be understood that the techniques described herein apply equally to single or more than two channels. The techniques works best when such multi-channel configuration illuminates and detects emission from the same location. Different channels are separated on the basis of wavelength or color, not by splitting the optical power of each color and thus obtainable sensitivity of the system is advantageously maintained.

Figures 2, 3A, 3B:
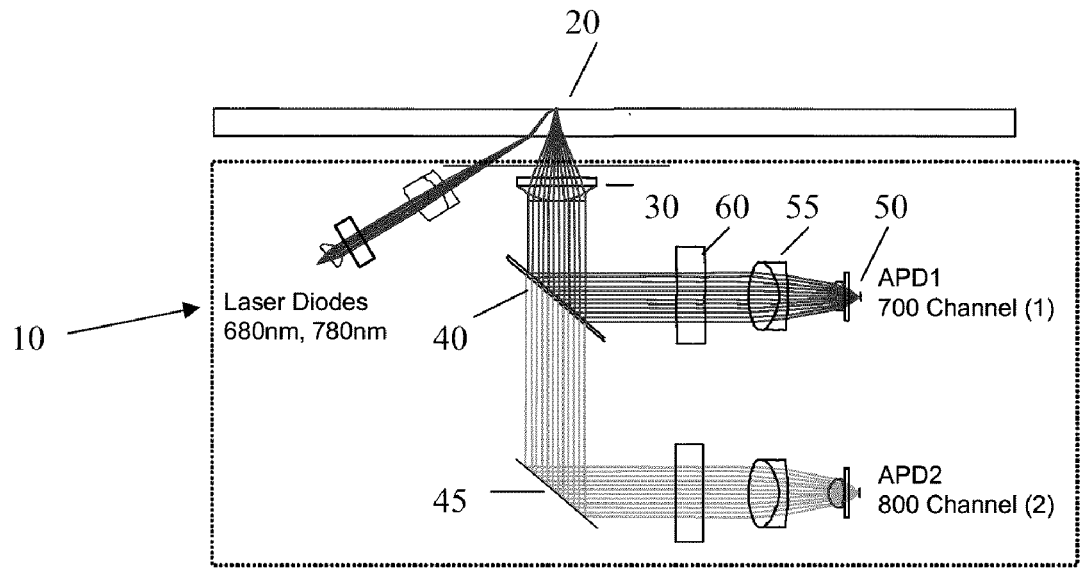
FIG. 2 illustrates an illumination and detection system according to one embodiment.
FIG. 3a shows an example of laser-power and detector gain settings with two scans using the system shown in FIG. 2.
FIG. 3b shows that scanning more than twice can also be achieved by using more than two settings for the excitation power and or detector gains (example: Low, Medium, and High) according to one embodiment.

One embodiment of an illumination and detection system 10 is depicted in FIG. 2. System 10 includes two illumination sources. Typically an illumination source includes a laser, however, other illumination sources may be used as desired. As shown, in one embodiment, the two illumination sources include laser diode devices configured to emit at two different frequencies or wavelengths (e.g., 680 nm and 780 nm as shown) and are configured to illuminate platform 20. The laser sources are typically packaged with TEC cooling, collimators, excitation filters, and combining optics to focus their output at the same target location on platform 20. It is also desirable to maintain the angular configuration of the Odyssey® design (U.S. Pat. No. 6,495,812) which avoids specular laser reflections, a significant element of low optical background that results in high dynamic range in a single measurement. The emitted fluorescence from both excitations (same location) is collected by an objective lens 30 and separated by a dichroic mirror 40 into two paths, each with maximum fluorescence from one excitation and minimum fluorescence from the other excitation. In each of these paths, fluorescence light is filtered further by emission filter(s) 60 and detected by a detector 50, e.g., an APD, set at an optimum gain setting. Additional optical elements may be included to facilitate direction and focus of light, such as mirror 45 and optical lens elements 55.

System 10 also includes an intelligence module (not shown), such as one or more processors, that is communicably coupled with the detectors 50. The intelligence module is adapted to receive and process signals from the detectors 50, e.g., signals representing, or proportional to, the detected illumination within the detectors' detection bandwidth. The intelligence module may automatically process the data and signals as received, or it may receive the data and signals and process subsequently, e.g., in response to a user command. An optional display device (not shown) is provided in certain embodiments to display data representative of various signals and images captured and/or processed by system 10. A memory module or device can also be provided to store data and code for use by the intelligence module, or for another system. For example, the memory may store code, executable by a processor, for implementing methods as disclosed herein, and/or data from the detectors and/or processor may be stored thereon. The memory may include a RAM or ROM, hard disk or any portable, non-transitory medium such as a DVD or CD.

According to one embodiment, a low channel cross-talk, extra-wide dynamic range scanning method includes scanning the same location twice: one time with the laser power and detector gain of one channel set to High and at the same time the laser power and detector gain of the other channel set to Low, e.g., Laser1_High, Detector1_High, Laser2_Low, and Detector2_Low, and another time with the settings reversed, e.g., Laser1_Low, Detector1_Low, Laser2_High, and Detector2_High. Then, for each of the two channels, a High scan and a Low scan are merged together to produce a wider dynamic range image, i.e., combine (Detector1_High and Detector1_Low) to obtain Ch1_merged and combine (Detector2_High and Detector2_Low) to obtain Ch2_merged.

More generally, a method according to one embodiment includes the following steps: a) scan the same location more than once, wherein at least one time, the power of the excitation light and detector gain are set to High for at least one of the channels and Low for at least one of the other channels and different settings are used in subsequent scans; b) merge scans of the same channel taken with different High and Low settings together to produce one wider dynamic range image.

Different color wide-dynamic-range images can further be combined in a multi-color image. FIG. 3a shows an example of laser-power and detector gain settings with two scans using the system shown in FIG. 2. Scanning more than twice (e.g., 3, 4 or more times) can also be achieved by using more than two settings for the excitation power and or detector gains (example for a 3 level scan: Low, Medium, and High) as shown in FIG. 3b. In this case the multiple scans taken for the same channel are merged together to produce one wider dynamic range image. In certain aspects, a subset of the scans for a single channel are merged to form a single image.

In certain aspects, the laser sources are modulated at modulation frequencies lower than the frequency of emitted illumination and the detectors are de-modulated at the modulation frequencies, respectively. For example, for a two channel configuration, first and second laser sources are modulated at first and second modulation frequencies, each lower than the frequency of illumination, and first and second detectors are de-modulated at the first and second modulation frequencies, respectively. For multiple channel configurations, each detector is de-modulated at the frequency of modulation of the corresponding laser source. The frequency of illumination is the optical frequency which corresponds to the wavelength of light (f=c/l), where c is speed of light and l is its wavelength. For visible light, for example, the frequency is about 5×10^14 Hz. The modulation frequency is the rate of turning the light source On-Off, e.g., turning the lasers On-Off through their drive currents). In one example, this rate is 8 kHz for one laser and 16 kHz for the other and they can be adjusted to any other two frequencies as long as they are less than 10^14 Hz.

Changing the laser power (that illuminates the target) between High and Low can be accomplished by changing the injection current for laser diodes or using optics, such as ND filters for other lasers. Other methods of changing power levels can also be used, such as changing a temperature of a diode laser and other methods as are known. Laser diodes are advantageous for a number of reasons and they also allow for a reliable, fast, easy way to switch between one or more levels of power that can span wide ranges. For example, one set Laser1_Low=2 mW and Laser1_High=20 mW giving a ratio of 10× increase/reduction in power levels. Laser2 can be set independently to different levels, for example: Laser2_Low=1 mW and Laser2_High=60 mW, a ratio of 60×. If wider dynamic range is desired, one can also change the detection gain, preferably electronic gain only for APDs. For example, Channel1_High/Channel1_Low and Channel2_High/Channel2_Low can be set to 10×, resulting in a total High/Low ratio for channel1=100× and for channel2=600×. Again, here, too, channels 1 and 2 can be set separately. Using 16 bit APDs, as in one embodiment, and scanning twice with the High and Low configuration described above produces for each channel two scans: one with high laser power and high electronic gain and one with low laser power and low electronic gain that are then merged according to that channel's High/Low ratio into an image of >>15 bit dynamic range. With the 100× and 600× ratios given above, the dynamic range of the merged images will be >20 bits and >23 bits, respectively. Even wider dynamic ranges can be achieved by re-scanning one or more times.

In general, for each illumination source a ratio of the high power setting to the low power setting should be about 2× or greater, or even 10× or greater, and for each detector a ratio of the high gain setting to the low gain setting should be about 2× or greater, or even 10× or greater.

An advantageous feature of the present system is that when the laser power and gain of one channel is set to High (i.e. during the sensitive scan for that channel), the other laser is set to Low and so the amount of cross-channel leakage from the channel is equally reduced. For example, for the 10× and 60× ratios given above, their channel cross-talk reductions are improved by 10× or 60×, respectively.

In one embodiment, each pixel location may be illuminated and detected for each laser power and detector gain setting before moving on to the next pixel location during a scan of multiple pixel locations. In a preferred embodiment, however, all of said plurality of pixels in a complete scan are illuminated and detected at the same laser power and detector gain setting before a scan is made at the next laser power and detector gain setting.

The merging of High and Low images from the same channel can be accomplished in a number of ways. According to one embodiment, saturated pixels in the High scan are replaced with a scaled copy of the respective pixel value from the Low scan. In one embodiment, a per-pixel linear regression fit between the High and Low values (and other values, e.g., Mid, for more than two channels) is performed to calculate the slope of the line that interpolates those values, where the slope of the line represents the merged pixel value. One way to represent this regression is as follows $$im(R) = im_{merged} \cdot R + \text{error}(R)$$

$$im_{merged} = \frac{1}{R_{Low}} \frac{im(R_{Low}) + im(R_{High}) \cdot \rho}{1 + \rho^2}$$

where R represents the response of the system. R is a factor representing the relative product of the laser power setting and the detector gain setting. For two settings, High and Low, R takes two values, $R_{Low}$ and $R_{High}$. $\rho$ is used to represent the ratio of $R_{High}/R_{Low}$. The obtained values for $im_{merged}$ are a measure of the change in signal level as the system's response, R, changes and covers the High and Low ranges. Therefore, it represents a scaled copy of a combined (merged), wider dynamic range image. In the actual calculation, $R_{Low}$ can be replaced by any desired number such as 1. Other ways to estimate the pixel values for the merged image can be used, including the use of weighting factors to scale down high pixel values that approach saturation. Some or all of the merged pixel values may be displayed as desired.

Figure 4:
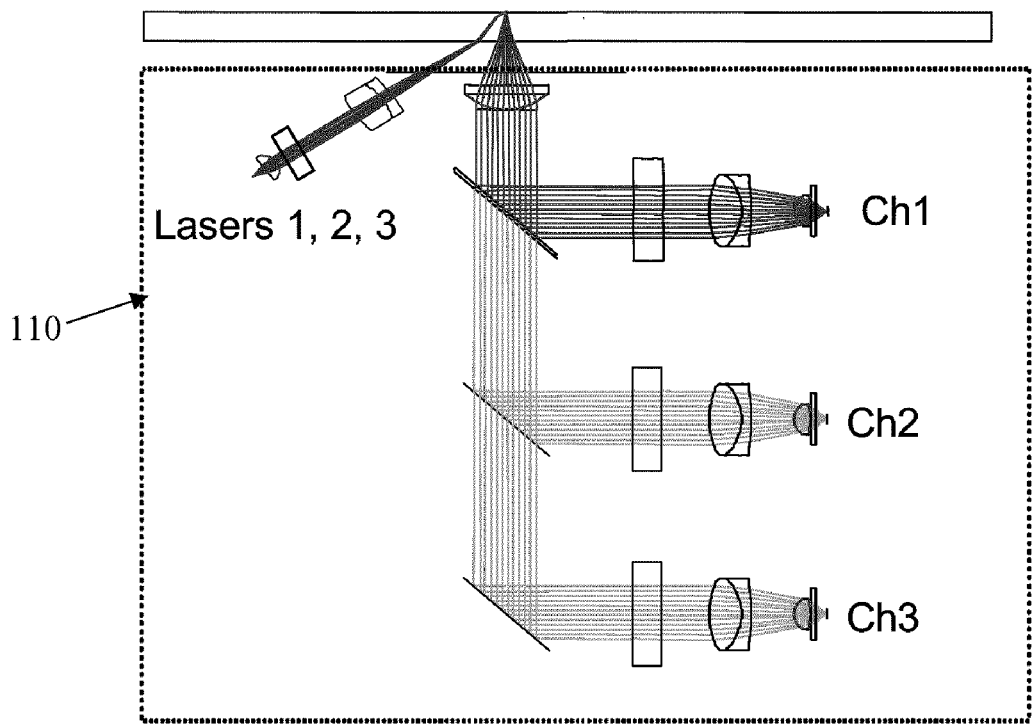
FIG. 4 shows a 3-channel system according to one embodiment.

The above equations can easily be expanded for the case of more than two scans and more than High/Low ratios. FIG. 4 shows a 3-channel system 110 according to one embodiment. As shown, system 110 includes three illumination sources, laser 1, laser 2 and laser 3, each configured to emit at a different excitation frequency, as well as the optical elements to direct and focus light from the platform onto the three detectors. As above, the three detectors are each adapted to detect at a different frequency bandwidth, corresponding to channel 1, channel 2 and channel 3, respectively. FIGS. 5a and 5b list example sets of settings for the scans and image groups to merge together.

FIG. 6a shows a merged scan of the same dilutions of FIG. 1a obtained by a one embodiment having a High/Low ratio of 135×. The original sensitivity is maintained and none of the previously saturated spot is now saturated, since now the linear dynamic range is extended by ~135×, more than 4 (2×) dilution spots. FIG. 6b shows a line profile across the dilution in region "A".

Also, a comparison of region "B" of FIG. 6a to region "B" in FIG. 1a shows that the channels cross-talk is reduced considerably, a direct benefit of lowering the laser power of the opposite channel. The remaining residual signal at those locations is primarily due to 780 nm laser exciting the 700DX dye and is small, as expected.

All US patents and applications mentioned herein are hereby incorporated by reference in their entirety for all purposes.

It should also be understood, that as used herein, the term wavelength or wavelengths (or frequency or frequencies) with reference to illumination sources and detectors means the wavelength (or frequency) range or ranges at which a source emits or at which a detector detects (or at which a fluorescent species emits). For example, a laser source may be said to emit at a certain specific wavelength, e.g., 680 nm, however, one skilled in the art understands that the specific wavelength refers to a wavelength bandwidth centered at the specific emission wavelength. Similarly, a detector detect over a range of wavelengths.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A method of reducing or eliminating cross talk in a fluorescence detection system having a first illumination source that emits illumination at a first illumination wavelength, a second illumination source that emits illumination at a second illumination wavelength, two detectors that detect at different wavelength ranges, and a sample platform having at least two fluorescent species, wherein a first fluorescent species absorbs light from the first illumination source and emits at a first fluorescence wavelength, and wherein a second fluorescent species absorbs light from the second illumination source and emits at a second fluorescence wavelength, the method comprising:
   a) in a first illumination and detection setting mode, wherein the first illumination source is set to a high power setting and a first detector is set to a high gain setting, and the second illumination source is set to a low power setting and a second detector is set to a low gain setting:
      i) simultaneously illuminating at least one of a plurality of pixel locations of the sample platform with illumination from the first and second illumination sources; and
      ii) simultaneously detecting a first intensity value for each detector, the first detector detecting at the first fluorescence wavelength range, and the second detector detecting at the second fluorescence wavelength range; and thereafter
   b) in a second illumination and detection setting mode, wherein the first illumination source is set to a low power setting and the first detector is set to a low gain setting, and the second illumination source is set to a high power setting and the second detector is set to a high gain setting:
      i) simultaneously illuminating the at least one pixel location with illumination from the first and second illumination sources; and
      ii) simultaneously detecting a second intensity value for each detector; and thereafter
   c) for each detector, processing the first and second intensity values to produce a merged image value for the at least one pixel location.

2. The method of claim 1, wherein processing includes performing a linear regression fit between the first and second intensity values to determine the merged image value for the pixel.

3. The method of claim 1, further including repeating steps a), b) and c) for each of the plurality of pixel locations on the sample platform.

4. The method of claim 3, wherein repeating includes repeating a) for all of said plurality of pixels, and then repeating b) for all of said plurality of pixels.

5. The method of claim 4, further including, for each detector, displaying a representation of the merged image values for some or all of said plurality of pixels.

6. The method of claim 1, wherein setting an illumination power includes filtering illumination emitted by a source to adjust the illumination power impinging on the sample platform.

7. The method of claim 1, wherein each of the first and second sources includes a diode laser, and wherein setting an illumination power includes changing an injection current of a diode laser.

8. The method of claim 1, wherein processing is performed responsive to receipt of a user input command to process.

9. The method of claim 1, wherein processing is performed automatically upon detection.

10. The method of claim 1, further including displaying a representation of the merged image value for the at least one pixel for each detector.

11. The method of claim 1, wherein the first and second sources are modulated at first and second modulation frequencies lower than the frequency of emitted illumination and wherein the first and second detectors are de-modulated at the first and second modulation frequencies, respectively.

12. A fluorescence detection system, comprising:
a first illumination source that emits at a first illumination frequency;
a second illumination source that emits at a second illumination frequency;
a first detector element configured to detect radiation at a first fluorescence frequency range;
a second detector element configured to detect radiation at a second fluorescence frequency range;
a target platform having a sample with two fluorescent species, wherein a first species absorbs illumination at the first illumination frequency and emits at the first fluorescence frequency, and wherein a second species absorbs illumination at the second illumination frequency and emits at the second fluorescence frequency;
optical elements configured to combine and focus illumination of the first and second sources onto the sample;
optical elements configured to direct and focus fluorescence light emitted by the sample onto the first and second detector elements; and
an intelligence module adapted to receive and process signals received from the first and second detectors,
wherein, during operation, at least one pixel location on the sample platform is simultaneously illuminated by the first and second sources in a first mode and in a second mode, and wherein fluorescence emitted by the first and second species is simultaneously detected by the first and second detectors in the first mode and in the second mode,
wherein in the first mode, the first illumination source is set to a high power setting and the first detector is set to a high gain setting, and the second illumination source is set to a low power setting and the second detector is set to a low gain setting, and
wherein in the second mode, the first illumination source is set to a low power setting and the first detector is set to a low gain setting, and the second illumination source is set to a high power setting and the second detector is set to a high gain setting,
wherein in the first mode, each detector outputs a first intensity value, and wherein in the second mode, each detector outputs a second intensity value, and
wherein the processor, for each detector, processes the first and second intensity values to produce a merged image value for the at least one pixel location.

13. The system of claim 12, wherein the processor applies a linear regression fit between the first and second intensity values to determine the merged image value for the at least one pixel location.

14. The system of claim 12, wherein each of a plurality of pixel locations on the sample platform are illuminated by the first and second sources in the first mode and in the second mode, and wherein fluorescence emitted by the first and second species is detected by the first and second detectors in the first mode and in the second mode, and wherein the processor, for each detector, processes the first and second intensity values to produce a merged image value for each of the plurality of pixel locations.

15. The system of claim 14, wherein all of said plurality of pixels are illuminated by the first and second sources in the first mode and then all of said plurality of pixels are illuminated by the first and second sources in the second mode.

16. The system of claim 15, further including a display device for displaying a representation of the merged image values for some or all of said plurality of pixels for each detector.

17. The system of claim 12, wherein each of the first and second sources includes a diode laser, the system further including means for changing an injection current of a diode laser so as to adjust an illumination power of the diode laser.

18. The system of claim 12, further including a means for filtering illumination emitted by a source so as to adjust the illumination power impinging on the sample platform.

19. The system of claim 12, further including a display device for displaying a representation of the merged image value for the at least one pixel for each detector.

20. The system of claim 12, wherein the first and second sources are modulated at first and second modulation frequencies lower than the frequency of emitted illumination and wherein the first and second detectors are de-modulated at the first and second modulation frequencies, respectively.

21. The system of claim 12, wherein for each illumination source a ratio of the high power setting to the low power setting is about 10 or greater, and wherein for each detector element a ratio of the high gain setting to the low gain setting is about 10 or greater.

22. A method of reducing or eliminating cross talk in a fluorescence detection system having two sources that emit illumination at different wavelengths, a sample platform having at least two fluorescent species and two detection channels, the method comprising:
a) setting the illumination power of a first source to a high power level and the illumination power of a second source to a low power level;
b) setting the gain of a first detector to a high gain level and the gain of a second detector to a low gain level;
c) simultaneously illuminating at least one of a plurality of pixel locations of the sample platform with illumination from the first and second sources, wherein a first fluorescent species absorbs light from the first source and emits at a first fluorescence wavelength, and wherein a second fluorescent species absorbs light from the second source and emits at a second fluorescence wavelength; and
d) simultaneously detecting a first intensity value for each detection channel, wherein a first detector detects the first fluorescence wavelength range and a second detector detects the second fluorescence wavelength range; and thereafter
e) setting the illumination power of the first source to a low power level and the illumination power of the second source to a high power level;
f) setting the gain of the first detector to a low gain level and the gain of the second detector to a high gain level;
g) simultaneously illuminating the at least one pixel location with illumination from the first and second sources;
h) simultaneously detecting a second intensity value for each channel; and thereafter
i) for each channel, processing the first and second intensity values to produce a merged image value for the at least one pixel location.

23. The method of claim 22, wherein for each source a ratio of the high power setting to the low power setting is about 10 or greater, and wherein for each detector a ratio of the high gain level to the low gain level is about 10 or greater.

24. The method of claim 22, wherein processing includes performing a linear regression fit between the first and second intensity values to determine the merged image value for the at least one pixel location.

25. The method of claim 22, further including repeating steps a) through h) for each of the plurality of pixel locations on the sample platform.

26. The method of claim 23, wherein repeating includes repeating a) through d) for all of said plurality of pixels, and then repeating e) through h) for all of said plurality of pixels.

27. The method of claim 24, further including, for each detector, displaying a representation of the merged image values for some or all of said plurality of pixels.

28. The method of claim 22, wherein setting an illumination power includes filtering illumination emitted by a source to adjust the illumination power impinging on the sample platform.

29. The method of claim 22, wherein each of the first and second sources includes a diode laser, and wherein setting an illumination power includes changing an injection current of a diode laser.

30. The method of claim 22, further including displaying a representation of the merged image value for the at least one pixel for each detector.

31. The method of claim 22, wherein the first and second sources are modulated at first and second modulation frequencies lower than the frequency of illumination and wherein the first and second detectors are de-modulated at the first and second modulation frequencies, respectively.

32. The method of claim 1, wherein for each source a ratio of the high power setting to the low power setting is about 10 or greater, and wherein for each detector a ratio of the high gain setting to the low gain setting is about 10 or greater.

* * * * *